United States Patent [19]

Deavenport et al.

[11] Patent Number: 5,041,585

[45] Date of Patent: Aug. 20, 1991

[54] PREPARATION OF ALUMINOXANES

[75] Inventors: Dennis L. Deavenport, Seabrook; James T. Hodges, III., Alvin, both of Tex.; Dennis B. Malpass, Peekskill, N.Y.; Nam H. Tran, Houston, Tex.

[73] Assignee: Texas Alkyls, Inc., Deer Park, Tex.

[21] Appl. No.: 534,913

[22] Filed: Jun. 8, 1990

[51] Int. Cl.$^5$ ............................................... C07F 5/06
[52] U.S. Cl. .................................................. 556/179
[58] Field of Search ........................................ 556/179

[56] References Cited

U.S. PATENT DOCUMENTS

| | | | |
|---|---|---|---|
| 3,300,458 | 1/1967 | Manyik et al. | 260/88.2 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,908,463 | 3/1990 | Bottelberghe et al. | 556/179 |
| 4,924,018 | 5/1990 | Bottelberghe et al. | 556/179 |
| 4,937,363 | 6/1990 | Bottelberghe et al. | 556/179 |
| 4,960,878 | 10/1990 | Crapo et al. | 556/179 |
| 4,968,827 | 11/1990 | Davis | 556/179 |

FOREIGN PATENT DOCUMENTS 1319746 1/1973 United Kingdom .

OTHER PUBLICATIONS

H. Sinn et al., "Transition Metals and Organometallics as Catalysts for Olefin Polymerizations", (1988) pp. 257-268.
62 Chem. Abstracts 2787dm (1965).
J. Inorg. Nucl. Chem., 1961, vol. 23, pp. 133-134.

Primary Examiner—Arthur C. Prescott
Assistant Examiner—Porfirio Nazario
Attorney, Agent, or Firm—Richard P. Fennelly; Louis A. Morris

[57] ABSTRACT

Aluminoxanes can be produced by contacting an organic solvent containing a trialkylaluminum compound with an atomized spray of water. If desired, a pore-formed aluminoxane can be present as a reaction moderator.

9 Claims, 1 Drawing Sheet

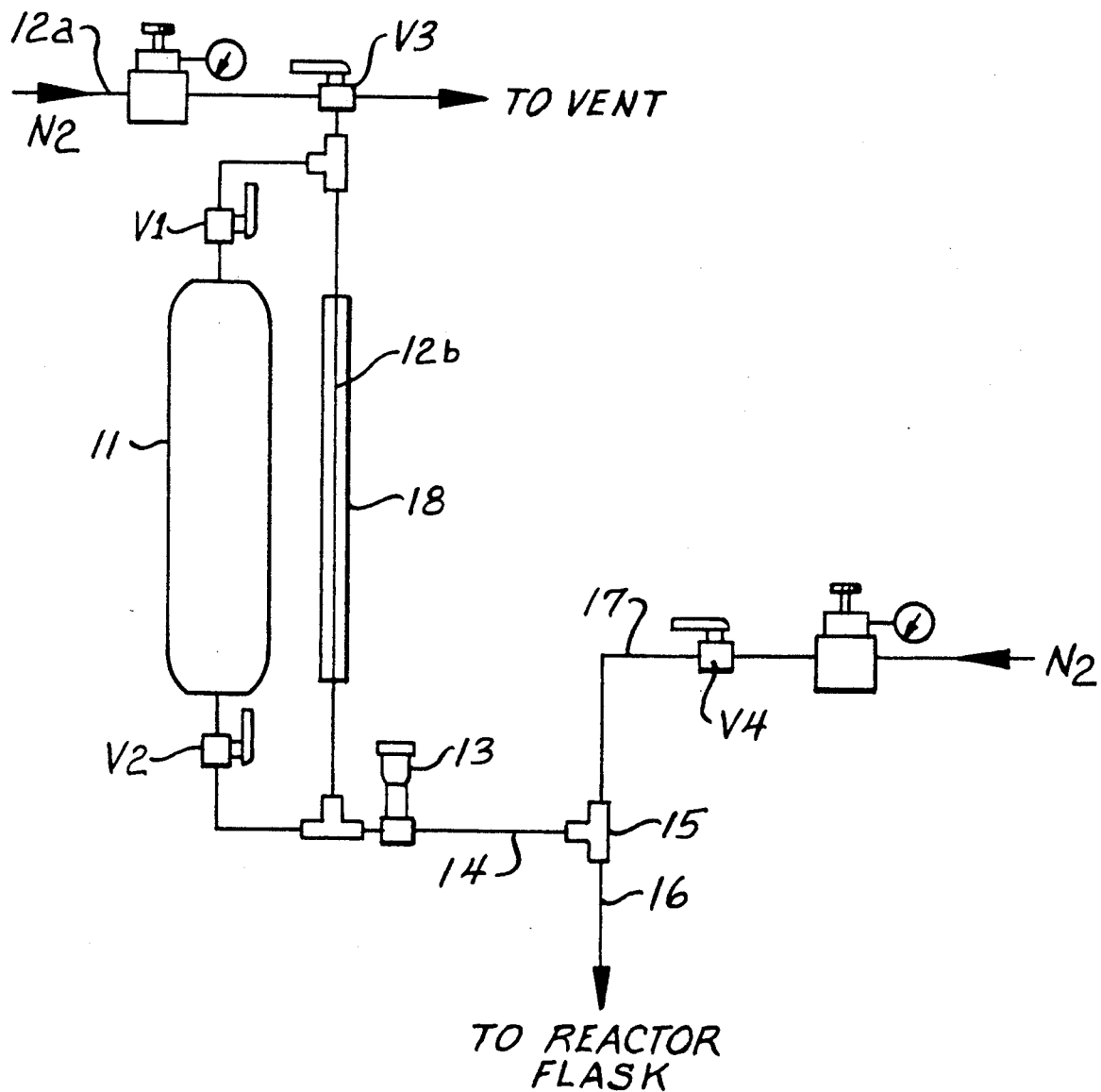

PREPARATION OF ALUMINOXANES

BACKGROUND OF THE INVENTION

It is well known that the preparation of aluminoxanes by reaction of a trialkylaluminum and water is very exothermic and requires great care in achieving the careful, controlled and incomplete hydrolysis of the trialkylaluminum to yield the desired product. Various method have been proposed to achieve this result including the general approach of contacting the water reagent in a controlled manner with the trialkylaluminum in a suitable organic solvent.

Use of hydrated salts, such as $CuSO_4\cdot 5H_2O$, $Fe(SO_4)\cdot 5H_2O$, or $Al_2(SO_4)_3\cdot 16H_2O$ has been employed as a means of controlling the reactivity of water with a trialkylaluminum (see, for example, U.S. Pat. Nos. 4,544,762 and 4,665,208).

U.S. Pat. No. 3,300,458 to R. M. Manyik et al. taught that a water-wetted solvent stream could be contacted with a calculated amount of an anhydrous solution of the trialkylaluminum reagent to bring about the reaction to produce the desired aluminoxane. Such an approach uses relatively large amount of solvent since two solvent streams, each combining one of the reactants, are used.

H. Sinn et al. in "Some New Results on MethylAluminoxane", "Transition Metals and Organometallics as Catalysts for Olefin Polymerization", W. Kaminsky et al. eds., Springer-Verlag, Berlin, Heidleberg, 1988, 257-268 indicates (on page 257) that Sakharovskaya et al. used "a nitrogen stream" as a carrier for the water vapor used in the reaction forming aluminoxanes. A careful analysis of the footnoted British Patent No. 1,319,746, however, fails to reveal such a teaching. The process suggested by this British citation involves the hydrolysis of trialkylaluminum with water in a tertiary alkyl amine medium. However, an earlier publication in 62 Chem. Abstr. 2787d (1965) speaks of the use of nitrogen containing moisture and oxygen in the reaction with a trialkylaluminum reagent.

S. Amdurski et al. in J. Inorg. Nucl. Chem., 1961, Vol. 23, pp. 133-134 indicates that the reaction between triethylaluminum and water can be suitably moderated by adding water "vapour" to the triethyl aluminum. A similar disclosure exists in J. Am. Chem. Soc. 90:12, June 1968, pp. 3173-3177 by A. Storr et al., in which a hydrolytic method is described (on pp. 3173-3174) in which water was provided to a limb of the apparatus apart from the section of the apparatus holding the solvent containing the alkylaluminum reagent. Warming of the limb holding the water turns it into a vapor which can diffuse into the solvent/aluminum alkyl solution.

More recently, U.S. Pat. Nos. 4,730,072 to G. W. Schoenthal et al. and 4,772,736 to D. N. Edwards et al. propose the use of a high degree of agitation within the solution to disperse a water stream when it comes into contact with the solution containing the trialkylaluminum reagent to thereby insure the desired controlled hydrolysis of the trialkylaluminum reagent. Analogously, U.S. Pat. No. 4,730,071 to G. W. Schoenthal et al. uses ultrasonic vibrational treatment of the organic solution containing the water to achieve dispersion of the water in the solvent medium.

Most recently, U.S. Pat. No. 4,908,463 to S. A. Bottelkerghe has suggested impinging a solution of a hydrocarbylaluminum in an inert solvent carrier with a water dispersion in an inert solvent in a T-shaped reactor. The highly turbulent water dispersion is formed by passing a solvent/water mixture through a static mixer.

SUMMARY OF THE INVENTION

The instant invention achieves the production of an aluminoxane product from an aluminum alkyl reagent by supplying the water reagent in the form of atomized liquid, rather than as a vapor, to an organic solvent holding the aluminum alkyl. The term "atomized liquid" as used herein in connection with the water reagent is to be construed as covering water in non-vaporized form in which small droplets of water exist, as liquid, in the physical form of a spray, mist, or fog. The atomized spray may be sprayed directly onto the surface of an agitated trialkylaluminum solution in hydrocarbon solvent or may be provided subsurface to such a solution thereby providing additional dispersion due to the vigorous bubbling action of the inert gas (e.g., nitrogen) carrier stream when such a carrier stream is used, as is preferred.

The instant invention differs in various ways from some of the foregoing means to combine a water reagent with the alkylaluminum reagent. Unlike the Manyik et al. patent it does not rely upon combining two solvent streams. It adds the water in the form of an atomized liquid rather than as a vapor as taught by Sakharovskaya et al., Amdurski et al., or Storr et al. Unlike the disclosure of the Schoenthal et al. or Edwards et al. patents, neither a high degree of mechanical agitation of the alkylaluminum solution or the use of ultrasonic vibrational treatment of the solution is needed. Reaction between the water and trialkylaluminum reagent takes place in the instant process over shorter periods of time as compared to the use of hydrated salts or the use of water vapor. The yield of product is also higher than those typically obtained using other techniques, especially the use of hydrated salts. The instant process has the advantage that "carriers" for the water reagent are not required and, therefore, do not have to be removed from the product during its use in polymerization. The instant process has the additional advantage of maintaining a constant solvent to product ratio as compared to the type of processes shown in U.S. Pat. Nos. 3,300,458 or 4,908,463, for example, which utilize fresh solvent as a carrier for the water needed in the reaction.

DESCRIPTION OF THE FIGURE

The FIGURE depicts one embodiment of an apparatus which can be employed in accordance with the present invention.

DETAILED DESCRIPTION OF THE INVENTION

The present invention reacts an aluminum alkyl reagent with water in a controlled manner, in an organic solvent medium, to achieve the production of an aluminoxane product. It is well known that the aluminoxane is useful as a component in polymerization and oligomerization catalysts. These aluminoxanes, as is well known, can be cyclic or linear.

The trialkylaluminum reagents known in the art as suitable for producing aluminoxanes upon appropriate reaction with water (e.g., the $C_1$-$C_5$ trialkylaluminum species). Representative examples include trimethylaluminum (the preferred reagent), triethylaluminum, triisopropylaluminum, tri-n-propylaluminum, triisobutylaluminum, tri-n-pentylaluminum, and the like. Mixtures may also be used.

The organic solvent medium used in accordance with the present invention is one which is substantially inert (e.g., non-oxygenated) to the hydrolysis reaction an is effective in dissolving the trialkylaluminum reagent so that it is available for controlled hydrolysis when atomized liquid water is contacted with it in accordance with the present invention. Examples include the saturated aliphatic solvents, the cycloaliphatics, the alkenes and cycloalkenes, and the aromatic solvents such as described in U.S. Pat. No. 4,730,071, for example.

The reaction temperature is advantageously kept below about 5-10° C., preferably below 0° C., e.g., $-15°$ C. to $-25°$ C. Pressure is not critical.

The invention depends upon the atomization of a stream of water and the feeding of the atomized spray to the solution containing the trialkylaluminum reagent which is to be hydrolyzed to form the aluminoxane. The use of a pre-atomized spray of water obviates the need to mechanically disperse the water in the solvent medium by either rapid stirring, ultrasonic vibrational energy, static mixing or the like to the degree taught in U.S. Pat. Nos. 4,730,071, 4,730,072, 4,772,736 or 4,908,463.

The FIGURE depicts apparatus which can be used to practice the process described herein. Water in reservoir 11 is pressurized (e.g., 80 psi) with nitrogen gas fed via lines 12a and 12b through an appropriate metering valve 13, line 14, T-shaped nozzle 15 and line 16 to a reactor flask (not shown) holding the aluminum alkyl reagent in a suitable solvent. Additional pressurized nitrogen gas (e.g., at 10-30 psi) is fed via line 17 to the T-shaped aspiration nozzle 15. The configuration of the T nozzle is designed such that water enters perpendicularly to the nitrogen stream from line 17. Other configurations of the inlet lines (i.e., angles of impingement, relative diameters of the two impinging tubes inside the T nozzle and configuration of the exit nozzle 16) may be varied within certain limits to achieve aspiration efficiencies from optimal to acceptable. The key concept is to generate and deliver a controllable mist of water in the nitrogen stream where the droplets are exceptionally small. Line 12b in the apparatus depicted in the FIGURE allows for an accurate monitoring of the water flow in the following manner. Valves V1 and V2 are both opened to fill the calibrated sight glass 18 in line 12b with water. Then valve V2 is closed and the rate of water addition can be accurately monitored by watching the water level drop in sight glass 18. By opening of valve V2, the water level drops in the sight glass. Closure of V2 gives an indication of the amount of water added at any given time. It is possible to use sight glass 18 in this manner to set the rate of water addition using metering valve 13 after which the two valves V2 and V4 are allowed to remain open for the duration of the run.

Comparison tests have shown that the material of construction of the exit nozzle 16 is important in achieving the best results with TEFLON fluoropolymer producing results which are superior to stainless steel of comparable length and internal diameter. The pressure of the exit stream (line 16) should be high relative to the external pressure to further enhance the atomization effect by virtue of turbulence at the nozzle tip produced by the rapidly expanding nitrogen stream. A fluoropolymer nozzle construction has an additional advantage when injection is subsurface since a non-sticking fluoropolymer surface prevents build-up of solids on the tip of the nozzle due to localized over-hydrolysis. Adhering particles are quickly removed as they are formed on the nozzle tip from the vibration and turbulence generated by normal operation of the apparatus.

It is contemplated that other apparatus (e.g., fog nozzles) which achieve the generation of a fine spray, mist or fog of liquid water are useful in regard to the instant invention.

The present invention is further illustrated by the Examples which follow.

EXAMPLE 1

This is illustrative of two batch processes for making methylaluminoxane by the instant invention.

Methylaluminoxane (MAO) as a 4.4 wt % Al solution in toluene (598 gm, 26.3 gm Al, 0.975 mole Al) was charged to a 4-necked 1-liter flask fitted with a condenser and a mechanical agitator. Then, trimethylaluminum (58.6 gm, 21.9 gm Al, 0.813 mole) and toluene (303 gm) were charged simultaneously to the flask. The solution was heated to reflux for an hour and cooled down to $-5°$ to $-10°$ C. Water (8.8 gm, 0.489 mole) with a H20/TMAL molar ratio of 0.6 was introduced to the solution as an atomized water spray. The reaction temperature was maintained between $-5°$ and $-10°$ C. by a dry ice/cold oil bath during the water addition. After the water charge was completed, the flask was heated up to 70-85° C. for 10 minutes. The solution was then allowed to cool down and settle overnight. Clear supernatant (887.1 gm) was removed and was analyzed for aluminum analysis and showed 4.61 wt% Al. The recovery yield was 84.7% based on aluminum recovery. The product showed the specific activity of $6.4 \times 10^4$ gm PE/(gm Zr atm $C_2H_4$ hr) in homogeneous Ziegler catalysis.

EXAMPLE 2

An additional amount of water was introduced to the methylaluminoxane solution from the previous batch to increase the ratio of $H_2O$/TMAL from 0.54 to 0.97. The yield was calculated as 79% and the specific activity was increased to $1.5 \times 10^6$ gm PE/(gm Zr atm $C_2H_4$ hr).

One additional batch was made at a $H_2O$/TMAL molar ratio of 0.6 using the same technique and conditions except for the reactor temperature ($-20°$ to $-25°$ C.) with approximately the same quantities. The yield was 80.9% and the specific activity was $1.2 \times 10^6$ gm PE/(gm Zr atm $C_2H_4$ hr). The second water addition was not required.

EXAMPLE 3

This illustrates a semi-continuous process in accordance with the present invention.

Methylaluminoxane (600 gm of 4.44 wt% Al MAO in toluene) and trimethylaluminum (14.23 gm, 0.197 mole) were charged under $N_2$ atmosphere to a 2-liter 4-necked flask fitted with a condenser and a mechanical agitator. The flask was submerged in a dry ice/cold oil bath. When the flask temperature dropped down to $-20°$ C., with agitator setting at high speed, trimethylaluminum, as a 26 wt% solution in toluene, was fed at the rate of 8 cc/min, and water was introduced simultaneously to the solution at the rate of 0.2 cc/min as an atomized water spray. The total trimethylaluminum and water fed into the reaction flask was 229 gm (3.18 moles) and 36.8 gm (2.04 moles), respectively. The $H_2O$/TMAL ratio was calculated as 0.64. The reaction mixture was then heated up to 70-80° C. for 10 minutes and residual solids were allowed to settle overnight. The clear supernatant (1234 gm), which was a soluble methylaluminoxane product, was removed from the flask and was analyzed for aluminum concentration. Analysis showed 7.29 wt% Al. The yield was calculated as 80% based on aluminum recovery. The polymer test showed the product having a specific activity of $1.6 \times 10^6$ gm PE/(gm Zr atm $C_2H_4$ hr) in homogeneous Ziegler catalysis.

EXAMPLES 4-6

Listed below are the conditions for three additional runs practiced in a batch manner:

| No. 4 | |
|---|---|
| TMAL/MAO Ratio: | 0.83 |
| $H_2O$/TMAL Ratio: | 0.60 |
| % Al (Calc.): | 5.06 |
| % Al (Actual): | 4.61 |
| % Yield: | 84.7 |
| Activity: | $6.4 \times 10^4$ |
| Rxn Temp.: | −5 to −10° C. |
| Injector Tip: | 2 inches above liquid |

There was little foaming. Solid particles coated the wall of the glassware and carried through the bubbler. It took about 1.5 hours to finish adding 8.8 grams of water.

| No. 5 | |
|---|---|
| TMAL/MAO Ratio: | 0.853 |
| $H_2O$/TMAL Ratio: | 0.54 |
| % Al (Calc.): | 5.07 |
| % Al (Actual): | 4.86 |
| % Yield: | 80.9 |
| Activity: | $1.2 \times 10^6$ |
| Rxn Temp.: | −20 to −25° C. |
| Injector Tip: | 2 inches above liquid |

There was less solids formation in this Example than in No. 4 as well as less carry over of particles to the bubbler. Less solids formed at the bottom of the flask as compared to Example 4.

| No. 6 | |
|---|---|
| TMAL/MAO Ratio: | 0.83 |
| $H_2O$/TMAL Ratio: | 0.97 |
| % Al (Calc.): | 4.20 |
| % Al (Actual): | 4.79 |
| % Yield: | 79.0 |
| Activity | $1.5 \times 10^6$ |
| Rxn Temp.: | −20° C. |
| Injector Tip: | 2 inches above liquid |

In this Example the reaction was conducted at a higher $H_2O$/TMAL ratio than in Example 4 and some solid was observed floating just beneath the surface of the liquid.

EXAMPLES 7-8

These represent continuous processes in which TMAL/toluene and water were added continuously to the reactor flask with a heel of methylaluminoxane solution in the flask.

| No. 7 | |
|---|---|
| $H_2O$/TMAL Ratio: | 0.64 |
| Rxn Temp.: | −20° C. |

| -continued | |
|---|---|
| Feed Rate: $H_2O$: | 0.20 cc/min |
| TMAL/toluene: | 8.0 cc/min |
| % Yield: | About 80% |
| Activity: | $1.6 \times 10^6$ |
| No. 8. | |
| $H_2O$/TMAL Ratio: | 0.80 |
| Rxn Temp.: | −20° C. |
| Feed Rate: $H_2O$: | 0.20 cc/min |
| TMAL/toluene: | 8.0 cc/min |
| % Yield: | About 40% |
| Activity: | $9.5 \times 10^5$ |

In Run No. 8 a significant amount of solid and gelatinous product was formed.

EXAMPLE 9

This experiment was conducted on a pilot plant scale whereby MAO was prepared in a 10 gallon reactor. This Example illustrates that MAO exhibiting high activity for production of polyethylene can be produced directly via the technique of the present invention in reasonably high yields in the absence of a heel of preformed MAO in toluene.

Anhydrous toluene (approx. 21.8 kg) and TMAL (approx. 0.91 kg) were added to the reactor. With an agitation rate setting at 160 rpm, the contents were cooled to −6° C. Water (146 gm, 8.11 moles) representing a $H_2O$/TMAL molar ratio of 0.55 was then introduced to the solution as an atomized water spray. With the maximum flow of refrigerating oil through the at from −6° C. to 0° C. throughout the water addition. The reactor pressure was kept at 15-17 psig during the water addition. The MAO solution was then concentrated by flash distilling toluene (18.2 kg) from the final MAO solution. A total amount of 3.58 kg of clear supernatant (containing 6.1 wt % Al) was collected by decantation from the reactor. The calculated yield of MAO based on starting TMAL was 65%. The product showed a specific activity of $1.1 \times 10^6$ gm PE/(gm Zr atm $C_2H_4$ hr) at standard polyethylene polymerization conditions.

The foregoing Examples, which illustrate certain preferred embodiments of the invention, should be taken as merely exemplary and should not be construed in a limiting sense. The scope of protection sought is set forth in the claims which follow.

We claim:

1. A process for the production of an aluminoxane which comprises contacting an organic solvent comprising at least one trialkylaluminum compound with atomized liquid water.

2. A process as claimed in claim 1 wherein the trialkylaluminum is trimethylaluminum.

3. A process as claimed in claim 1 wherein the solvent is an aromatic solvent.

4. A process as claimed in claim 3 wherein the trialkylaluminum is trimethylaluminum.

5. A process for the production of an aluminoxane as claimed in any of claims 1-4 wherein the organic solvent also contains a pre-formed aluminoxane reaction moderator.

6. A process as claimed in claim 5 wherein the moderator is dialkylaluminoxane.

7. A process as claimed in claim 5 wherein the moderator is a polyalkylaluminoxane.

8. A process as claimed in any of claims 6-7 wherein the alkyl moiety in the aluminoxane is methyl.

9. A process as claimed in any of claims 1-4 where the atomized liquid water is injected below the surface of the organic solvent containing the trialkylaluminum compound.

* * * * *